(12) United States Patent
Hofvander et al.

(10) Patent No.: US 8,255,169 B2
(45) Date of Patent: Aug. 28, 2012

(54) BINNING AND TOMOGRAPHY FOR HIGH SPATIAL RESOLUTION TEMPERATURE AND SPECIES CONCENTRATION MEASUREMENTS

(75) Inventors: Henrik Hofvander, Boulder, CO (US); Andrew D. Sappey, Lakewood, CO (US); James Howell, Louisville, CO (US); Qingchun Zhao, Longmont, CO (US)

(73) Assignee: Zolo Technologies, Inc., Boulder, CO (US)

( * ) Notice: Subject to any disclaimer, the term of this patent is extended or adjusted under 35 U.S.C. 154(b) by 257 days.

(21) Appl. No.: 12/600,034

(22) PCT Filed: May 23, 2008

(86) PCT No.: PCT/US2008/064703
§ 371 (c)(1),
(2), (4) Date: Nov. 13, 2009

(87) PCT Pub. No.: WO2008/147994
PCT Pub. Date: Dec. 4, 2008

(65) Prior Publication Data
US 2010/0241361 A1    Sep. 23, 2010

Related U.S. Application Data

(60) Provisional application No. 60/940,006, filed on May 24, 2007.

(51) Int. Cl.
*G01N 31/00* (2006.01)
*G01R 13/00* (2006.01)
(52) U.S. Cl. ............. 702/24; 702/66; 702/189; 702/190

(58) Field of Classification Search .................... 702/24, 702/66–76, 189–190
See application file for complete search history.

(56) References Cited

U.S. PATENT DOCUMENTS
6,015,969 A * 1/2000 Nathel et al. ............ 250/227.27
2006/0181710 A1 * 8/2006 Kachanov et al. ............ 356/437

FOREIGN PATENT DOCUMENTS
CN         1945287 A       4/2007

OTHER PUBLICATIONS

Liu, et al., Feb. 2007, AIAA Journal, vol. 45, No. 2, p. 411-419, "Measurement of Nonuniform Temperature Distributions Using Line-of-Sight Absorption Spectroscopy".
International Search Report dated Aug. 8, 2008 for PCT/US2008/064703.
Chinese Office Action dated Mar. 22, 2011 with English Translation of corresponding Chinese patent application No. 200880017330.4.

\* cited by examiner

*Primary Examiner* — Phuong Huynh
(74) *Attorney, Agent, or Firm* — Swanson & Bratschun, L.L.C.

(57) ABSTRACT

A method of absorption spectroscopy including obtaining absorption data at multiple wavelengths along more than one line-of-sight path through a quantity of gas of interest. The method further includes identifying more than one temperature and gas species concentration bin along the multiple line-of-sight paths and creating a map of temperature and gas species concentration. The map thus created will have at least two-dimensional information derived from select temperature and gas species concentration bins identified along more than one line-of-sight path. Apparatus for implementing the above method is also disclosed.

9 Claims, 12 Drawing Sheets

BINNING AND TOMOGRAPHY FOR HIGH SPATIAL RESOLUTION TEMPERATURE AND SPECIES CONCENTRATION MEASUREMENTS

RELATED APPLICATIONS

This application is a 35 U.S.C. §371 national phase application of PCT/US2008/064703(WO 2008/147994), filed on May 23, 2008 entitled "Binning and Tomography for High Spatial Resolution Temperature and Species Concentration Measurements", which application claims the benefit of U.S. Provisional Application Ser. No. 60/940,006, filed May 24, 2007, each of which applications are incorporated herein by reference in their entirety, for all matters disclosed therein.

TECHNICAL FIELD

The present invention is directed toward a method and apparatus for obtaining high spatial resolution spectroscopic gas temperature and species concentration measurements through binning and tomography.

BACKGROUND

Absorption spectroscopy, including tunable diode laser absorption spectroscopy (TDLAS) are techniques for measuring the concentration of various species in a gaseous mixture. Absorption spectroscopy techniques are particularly well-suited to achieve very low detection limits. In addition to species concentration, it is possible with absorption spectroscopy to determine the temperature, pressure, velocity and mass flux of certain species of the gas under observation.

A typical TDLAS apparatus includes a tunable diode laser light source plus emission and receiving optics and detectors. The output of the tunable diode laser is tuned over a wavelength range encompassing selected absorption lines of various gas species of interest in the path of the laser beam. Absorption features cause a reduction of measured signal intensity which can be detected and used to determine gas concentration and other properties. The use of TDLAS is described in detail in co-pending U.S. patent application Ser. No. 10/543,288 entitled "Method And Apparatus For The Monitoring And Control Of Combustion", which application is incorporated herein by reference in its entirety.

Tomography is a technique whereby spatial resolution is obtained from line-of-sight measurements over multiple, often intersecting paths or projections, at a variety of selected orientations. Tomography is a well-known technique which has been used extensively in applications such as medical imaging. At each orientation, the transmitted radiation is monitored. Each transmission measurement is an average over the path traversed by the beam. In other words, an individual projection provides no spatial information. Using the transmission results from many projections as inputs allows the use of mathematical transforms to reconstruct what the object must look like in order to produce the measured transmissions. In this way, spatial resolution is obtained from a technique that intrinsically produces a line-of-sight average. High tomographic spatial resolution requires that many projections be used. In the case of absorption spectroscopy applications the required optical access may not be available to support many beam paths thus limiting traditional tomography to relatively low resolution. In other cases, cost considerations may limit the number of possible beam paths also limiting the obtainable resolution.

Temperature binning is a second known absorption spectroscopy technique where a certain degree of spatial resolution can be achieved for temperature measurements taken along a single line-of-sight projection. See, for example, "Measurement of Nonuniform Temperature Distributions Using Line-of-Sight Absorption Spectroscopy" by Liu, Jeffries & Hanson (February 2007, AIAA Journal, 45:2:411) (Appendix II), which article is incorporated by reference herein in its entirety. Temperature binning techniques may supplement conventional TDLAS measurements to determine variations in temperature over a single beam path. For example, with conventional TDLAS a path averaged temperature may be determined by measuring absorption over two carefully-chosen wavelengths of the same combustion species. Sensitive temperature measurements can be made if the transmission intensity of the two chosen spectral features are known to behave differently as the temperature changes. The ratio of the intensity of the absorption features is particularly well suited as an indicator of temperature, since the ratio does not depend upon species concentration as does the measured intensity of each individual line. Thus accurate temperature measurements may be made with TDLAS based apparatus even though actual species concentration is initially unknown.

Temperature binning is similar to conventional two line temperature measurement, but the use of multiple absorption lines permits the determination of the relative length of more than one temperature zone along the line-of-sight path; the zones are known as temperature bins. For most combustion systems, water provides a convenient target species since it is ubiquitous in combustion systems and it absorbs strongly at readily accessible wavelengths. However, oxygen or any other species can be used as the target molecule in alternative gas systems as well. In most combustion systems, the temperature varies greatly over the path of any single projection. In summary, temperature binning involves the use of multiple wavelengths to identify bins of length $L_1 \ldots L_n$, where each defined bin is at an average temperature of $T_1 \ldots T_n$. In general, every additional bin requires that at least two new wavelengths be used to make the measurement. In cases where the species concentration of the target is not known, more than two wavelengths must be added to define every new bin.

Many temperature bins can be defined as long as a sufficiently large number of appropriate wavelengths are used for the measurement; however, the temperature binning technique has one notable shortcoming; binning does not provide information regarding how each bin is arranged spatially with respect to the other bins. Sometimes this information can be gained from a priori knowledge of the gas or combustion system. For example, relatively cool transition zones are often located at the edges of a combustion system. A priori knowledge may however lead to erroneous conclusions in certain instances, for example in the case of malfunctioning combustors or poorly understood gas systems.

The present invention is directed toward overcoming one or more of the problems discussed above.

SUMMARY OF THE EMBODIMENTS

One embodiment is a method of absorption spectroscopy including obtaining absorption data at multiple wavelengths along more than one line-of-sight path through a quantity of gas of interest. The method further includes identifying more than one temperature and gas species concentration bin along the multiple line-of-sight paths and creating a map of temperature and gas species concentration. The map thus created will have at least two-dimensional information derived from select temperature and gas species concentration bins identified along more than one line-of-sight path.

The method described above may further include determining the spatial location of a select temperature and gas species concentration bin by comparing the bins identified along one line-of-sight path with the bins identified along an intersecting line-of-sight path. The distribution of temperature and species concentration may be expressed as an analytical function of position corresponding to at least two line-of-sight paths. Alternatively, the distribution of temperature and species concentration may be expressed as a series of discrete values along at least two line-of-sight paths.

An alternative embodiment is an apparatus for absorption spectroscopy including apparatus for obtaining absorption data at multiple wavelengths along more than one line-of-sight path through a quantity of gas of interest. The apparatus further includes spectroscopic analysis and data process equipment to identify more than one temperature and gas species concentration bin along the multiple line-of-sight paths and create a map of temperature and gas species concentration. The map thus created will have at least two-dimensional information derived from select temperature and gas species concentration bins identified by the apparatus along more than one line-of-sight path.

DETAILED DESCRIPTION OF THE EMBODIMENTS

Figure 1:
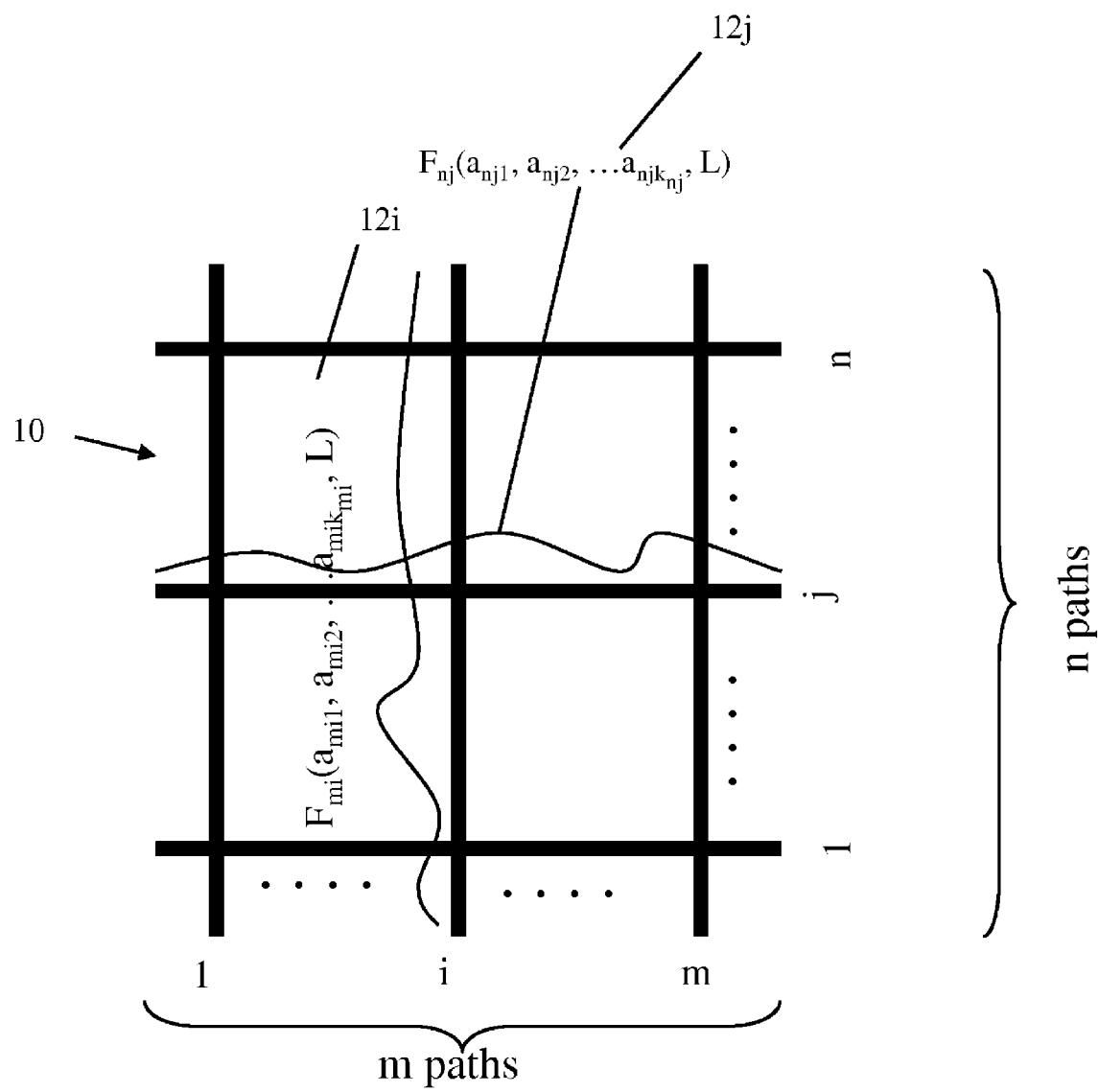
FIGS. 1-3 are schematic representations of select line-of-sight path layouts consistent with the present invention.

One embodiment disclosed herein is a method of performing absorption spectroscopy which combines tomography with temperature binning to improve multidimensional spatial temperature and species concentration resolution. In addition, the combination of tomography with temperature binning may provide certain necessary initial spatial information to deduce the order of the temperature bins determined to lie along any particular line-of-sight path without the need for a priori assumptions about the gas system being probed. Thus, the combination of tomography with temperature binning is symbiotic; the binning techniques may be used to increase tomographic resolution and tomography provides initial spatial information concerning the ordering of the temperature and species concentration bins measured along each line-of-sight path.

Certain methods disclosed herein feature spectroscopy along a select number of line-of-sight paths through a quantity of gas which is being probed. In addition, each line-of-sight path is spectroscopically probed at multiple wavelengths which correspond to multiple absorption lines associated with more than one transition of the gas species being probed. The embodiments disclosed herein are not limited to any particular tomographic pattern or number of bins. The techniques described herein can be used with any gas system, including but not limited to combustion systems, jet engines, conventional engines, rockets and laboratory or industrial gas systems. All embodiments feature absorption spectroscopy the key elements of which may be summarized as follows.

When laser light having the correct frequency is passed through a gas sample, the fraction of light that is absorbed can be predicted according to Einstein's theory of radiation. When a gas medium is uniform, the fraction of absorbed laser light may be calculated according to the Beer-Lambert Law:

$$\left(\frac{I_t}{I_0}\right)_v = \exp[-PX_{abs}S_i(T)\phi_v L] \quad \text{Equation \#1}$$

Definitions
$I_t$=transmitted laser intensity, W/m$^2$
$I_v$=laser intensity at frequency v, W/m$^2$
$I_0$=incident laser intensity, W/m$^2$
k=Boltzmann's constant, J/K
L=total path length, cm
P=total pressure, atm
$S_i$=line strength of transition i, cm$^{-2}$ atm$^{-1}$
T=temperature, K
$X_{abs}$=mole fraction of the absorbing species
$\phi_v$=line-shape function at frequency v The above relationship requires that the temperature T of the absorbing species be known. However, temperature may be measured based upon the fact that the line strength S is a function of temperature alone. Where two different absorption lines for the same species are probed while sweeping the absorption spectrum, the ratio of the integrated absorptions is a function of temperature alone according to Equation #2:

$$R = \frac{A_1}{A_2} = \frac{S_1(T)}{S_2(T)} \quad \text{Equation \#2}$$

Additional Definitions:
A=integrated absorbance, cm$^{-1}$
R=ratio of the integrated absorbances As described above, temperature binning utilizes the relationship of Equation 2 over multiple transitions with different temperature dependencies to determine information concerning a non-uniform temperature distribution along a select line of sight. The methods disclosed herein provide that the distribution of temperature and concentration of a target species may be expressed by either an analytical function of position or a series of discrete values along a given line-of-sight path. In the case of an analytical function of position, the coefficients of the analytical expression(s) may be solved through the binning techniques described above and tomography applied subsequently to map the temperature and species concentrations over the area under consideration. In the alternative case where discrete values are determined, each value is calculated through conventional TDLAS plus binning techniques for both temperature distribution and species concentration. Each value forms a temperature and species concentration bin with a specific size. A temperature distribution and species concentration map may thus be prepared by supplementing the binning information with tomographic data.

An example of absorption spectroscopy implemented with binning and tomography using analytical functions of position is schematically illustrated in FIG. 1. It is important to note that the illustration of FIG. 1 and the subsequent figures are not limiting upon the scope of the presently disclosed methods and apparatus. The particular tomographic and binning arrangements illustrated and described are representative examples selected to fully describe the binning and tomography strategies which can be implemented to achieve desired resolution goals. The methods and apparatus described herein may be implemented with any tomographic pattern including any number of or any arrangement of line-of-sight paths and any achievable number of bins. The final resolution obtained when implementing the methods described herein will be limited by only the number of paths used in the tomographic implementation and the number of wavelengths corresponding to absorption features available for measurement.

FIG. 1 is an orthogonal layout 10 of m paths by n paths which paths may be arranged for discussion in a rectilinear grid of any dimension having a total of m+n paths. The temperature and species concentrations represented in FIG. 1 are represented with an analytical function of position 12 along each path. Generally, the analytical function of position is in the form of $F(a_1, a_2, \ldots a_k, L)$, where F is a function of coefficients $a_1, a_2, \ldots$ and $a_k$ and L is the position. The number of coefficients for one selected path can be different than for other paths. The specific expressions shown in FIG. 1 are functions 12(i) for path i among m paths and function 12(j) for path j among n paths. The function 12 itself can be of any analytical form describing position and may be different from path to path. In general though, the simplest analytical function (the one requiring the fewest number of coefficients) should be used as this minimizes the number of simultaneous equations that must be solved and consequently provides the maximum amount of information for the number of wavelengths used. The coefficients for the functions 12 over all of the paths need to be solved using spectral absorption information measured at each wavelength plus any known boundary conditions for each path. With the temperature and species concentration distribution along each path determined, the temperature and concentration distribution at other points not directly on a path can be calculated by any suitable mathematical interpolation method. For example, a weighted average over the on-path points surrounding an off-path point could be used to calculate an estimation of the value at the off-path point. Other more sophisticated off-path estimation methods could be used as well.

Figure 2:
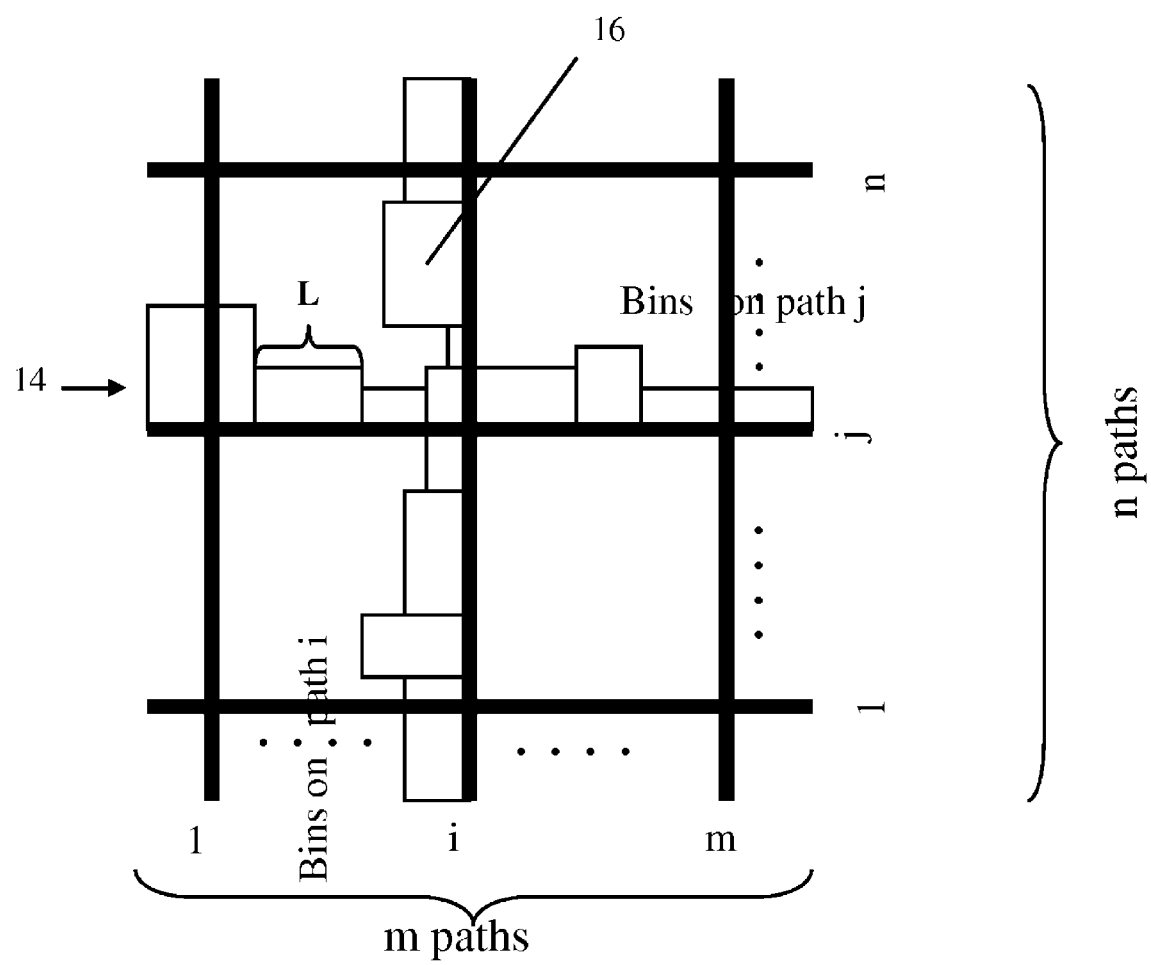

FIG. 2 is also a schematic layout 14 of n by m orthogonal paths which paths can be arranged in a rectilinear grid of any dimension (that sums to a total of n+m paths). In FIG. 2, the temperature and species concentrations are represented with discrete bins 16 having discrete values along portions of each path. Each temperature and concentration value is assumed constant over a certain length, L, the length of the bin. Different bins may have the same values and sizes, if appropriate. Initially, the ordering of bins along a given path is unknown. After all of the discrete values are solved for all the paths using conventional TDLAS and binning techniques, bin order may be deduced using observed bin information from adjacent or intersecting paths. Subsequently, a tomographic image may be created using any mathematically valid means of interpolation. For example, a weighted average over the paths around one off-path point gives rise to a reasonable estimate of the value at that point.

The present methods include two separate non-exclusive methodologies to solve the coefficients where an analytical function of position is created, or to solve each bin if discrete values are employed. The methodologies are a spectral absorption based methodology and a spectral profile based methodology each of which is described in detail below.

Spectral Absorbance Based Methodologies

The spectral absorption based methodologies solve for the values within each bin using absorption equations derived from the Beer-Lambert law (Equation 1), where the coefficients of an analytical function of position or the bin values/size are unknowns. The resulting calculated absorbances of each bin (which depends upon the assumed concentration, temperature, and bin length) are summed and must equal the measured total integrated absorbance along that path for each wavelength. The total integrated absorbance of each spectral line employed along each path is determined using generally known Beer-Lambert law techniques where Equation 1 is solved for absorbance; for example:

$$A = \int ln(I(\lambda)/I_0(\lambda)) d\lambda \qquad \text{Equation \#3}$$

To determine a unique solution, whether the temperature and concentration are expressed as an analytical function of position or a series of discrete values along a line-of-sight path, the number of unknowns must be equal to or less than the number of equations. In implementations where boundary conditions are known or a priori information concerning species concentration or temperature distribution is available and accurate, the number of equations may be increased without increasing the number of unknowns. Table 1 below includes a non-exclusive list of representative analysis scenarios with various practical assumptions which may be made to solve the spectral absorption data where temperature and concentration are expressed as a series of discrete values. Alternative scenarios where temperature distributions and species concentrations are expressed as analytical functions of position are discussed after Table 1.

TABLE 1

Representative Equations for Discrete Value Cases
Number of equations: $(p + q) * r$, r: number of spectral lines
Assumptions: $p \times q$ path arrangement with corresponding $m \times n$ bin arrangement. Total path lengths are known. T-bin temperature, L-bin length, C-bin concentration.

| Solutions with additional assumptions such as temperature boundaries, species uniformity and bin length arrangement along paths | Number of each variables<br>T's: number of temperatures;<br>L's: number of sizes;<br>C's: number of species concentrations. | Total variables and an instance |
|---|---|---|
| No temperature boundary conditions, non-uniform concentration and bin length variable among paths in parallel. | T's = p * n + q * m − p * q,<br>L's = p * n + q * m − p − q,<br>C's = p * n + q * m − p * q | Total variables: 3p * n + 3q * m − 2p * q − p − q. In the case of 2 × 2, p = q = 2.<br>Variables: 6n + 6m − 12. Equations: 12. From 6n + 6m − 12 = 12, get<br>n + m = 4. |

TABLE 1-continued

Representative Equations for Discrete Value Cases
Number of equations: $(p + q) * r$, r: number of spectral lines
Assumptions: $p \times q$ path arrangement with corresponding $m \times n$
bin arrangement. Total path lengths are known. T-bin temperature,
L-bin length, C-bin concentration.

| Solutions with additional assumptions such as temperature boundaries, species uniformity and bin length arrangement along paths | Number of each variables T's: number of temperatures; L's: number of sizes; C's: number of species concentrations. | Total variables and an instance |
|---|---|---|
| No temperature boundary conditions, uniform concentration and bin length variable among paths in parallel. | T's = $p * n + q * m - p * q$, L's = $p * n + q * m - p - q$, C's = 1 | Total variables: $2p * n + 2q * m - p * q - p - q + 1$. In the case of $2 \times 2$, $p = q = 2$. Variables: $4n + 4m - 7$. Equations: 12. From $4n + 4m - 7 = 12$, get $n + m = 4$. |
| No temperature boundary conditions, non-uniform concentration and same bin length arrangement among paths in parallel. | T's = $p * n + q * m - p * q$, L's = $m + n - 2$, C's = $p * n + q * m - p * q$ | Total variables: $2p * n + 2q * m - 2p * q + m + n - 2$. In the case of $2 \times 2$, $p = q = 2$. Variables: $5n + 5m - 10$. Equations: 12. From $5n + 5m - 10 = 12$, get $n + m = 4$. |
| No temperature boundary conditions, uniform concentration and same bin length arrangement among paths in parallel. | T's = $p * n + q * m - p * q$, L's = $m + n - 2$, C's = 1 | Total variables: $p * n + q * m - p * q + m + n - 1$. In the case of $2 \times 2$, $p = q = 2$. Variables: $3n + 3m - 5$. Equations: 12. From $3n + 3m - 5 = 12$, get $n + m = 5$. |
| With temperature boundary conditions, non-uniform concentration and bin length variable among paths in parallel. | T's = $p * n + q * m - p * q - 2p - 2q$, L's = $p * n + q * m - p - q$, C's = $p * n + q * m - p * q$ | Total variables: $3p * n + 3q * m - 2p * q - 3p - 3q$. In the case of $2 \times 2$, $p = q = 2$. Variables: $6n + 6m - 20$. Equations: 12. From $6n + 6m - 20 = 12$, get $n + m = 5$. |
| With temperature boundary conditions, uniform concentration and bin length variable among paths in parallel. | T's = $p * n + q * m - p * q - 2p - 2q$, L's = $p * n + q * m - p - q$, C's = 1 | Total variables: $2p * n + 2q * m - p * q - 3p - 3q + 1$. In the case of $2 \times 2$, $p = q = 2$. Variables: $4n + 4m - 15$. Equations: 12. From $4n + 4m - 15 = 12$, get $n + m = 6$. |
| With temperature boundary conditions, non-uniform concentration and same bin length arrangement among paths in parallel. | T's = $p * n + q * m - p * q - 2p - 2q$, L's = $m + n - 2$, C's = $p * n + q * m - p * q$ | Total variables: $2p * n + 2q * m - 2p * q - 2p - 2q + m + n - 2$. In the case of $2 \times 2$, $p = q = 2$. Variables: $5n + 5m - 18$. Equations: 12. From $5n + 5m - 18 = 12$, get $n + m = 6$. |
| With temperature boundary conditions, uniform concentration and same bin length arrangement among paths in parallel. | T's = $p * n + q * m - p * q - 2p - 2q$, L's = $m + n - 2$, C's = 1 | Total variables: $p * n + q * m - p * q - 2p - 2q + m + n - 1$. In the case of $2 \times 2$, $p = q = 2$. Variables: $3n + 3m - 13$. Equations: 12. From $3n + 3m - 13 = 12$, get $n + m = 8$. |

If the distribution of temperature and species concentration is expressed as an analytical function of position, the largest number of coefficients that can be determined is equal to the number of equations that can be solved. If one has a priori knowledge of certain aspects of the quantity of gas under-examination, it is possible that more coefficients can be determined with fewer equations. In certain cases, both an analytical function of position and a series of discrete values can be combined to accomplish binning if a priori information is available.

Once the distribution of temperature and species concentration is expressed as a series of discrete values (either initially or after solving analytical functions of position), a list of groups of temperature, species concentrations and bin size are determined. However, knowledge of the characteristics of the quantity of gas under examination may be required in order to arrange the bins along a given path. Once the binning is completed along intersecting or adjacent paths however and a priori conditions are considered, a tomographic representation of gas temperature and concentration may be created using mathematical calculations to fill in the voids between bins.

Spectral Profile Based Methodologies

The spectral profile based methodology of solving for the necessary coefficients when the distribution of temperature and species concentration is expressed as either an analytical function of position or a series of discrete values along a line-of-sight path includes directly binning unknowns to fit the characteristics of measured spectral profiles. Generally, the number of unknowns must be less than the number of data points measured in the spectrum and in most cases the number of unknowns must be significantly less than the number of spectral data points. Any suitable method, for example a minimum-square-error based algorithm may be used for purposes of fitting the measured spectral data to temperature and concentration bins. Once the binning unknowns are determined, a tomographic image may be created in the same way as in the spectral absorbance based methodology described above.

The measured spectral profile of a system under examination may not be as stable as the absorbance that is determined from the spectral profile. Consequently, the spectral profile based solution method is possibly better suited to an environment where the spectral signal is strong and stable and spectral change is readily measured. Alternatively, the spectral absorbance based solution method can be used in any measurement environment.

EXAMPLES

The following examples are provided for illustrative purposes only and are not intended to limit the scope of the invention.

Example 1

Figure 3:
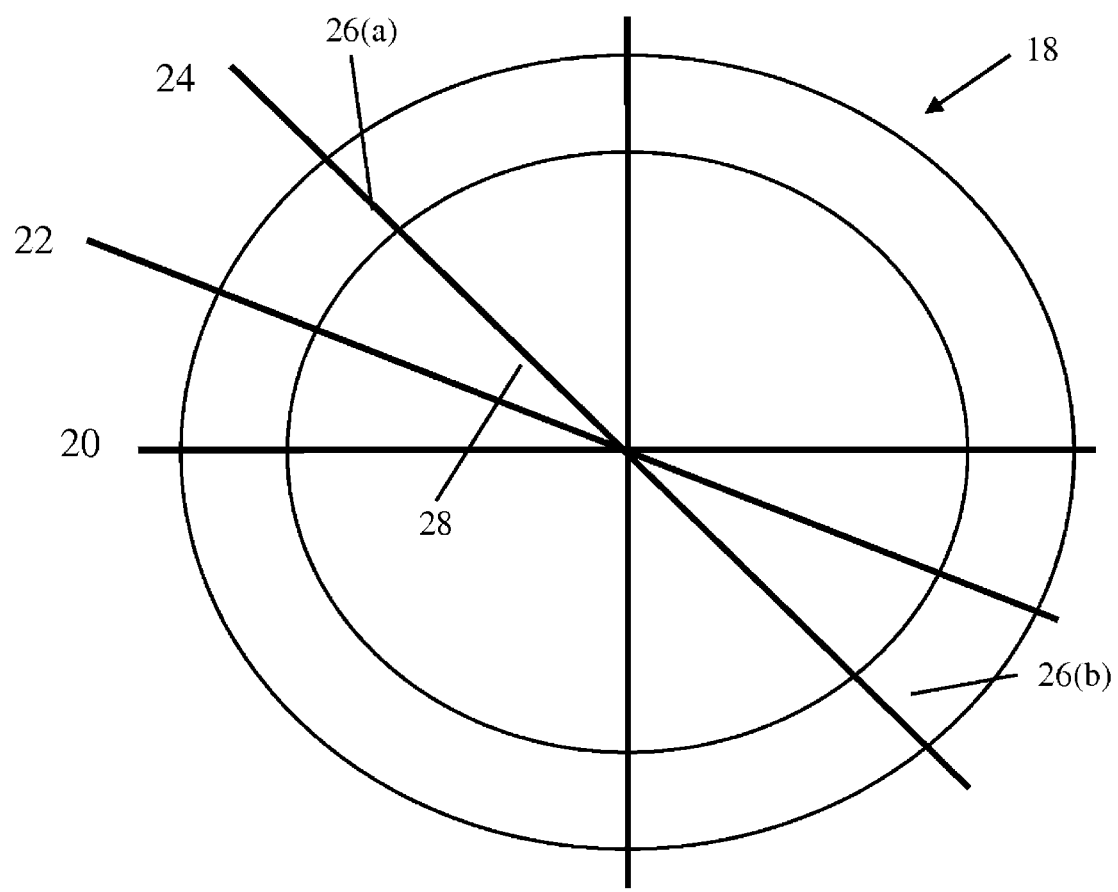
Figure 4:
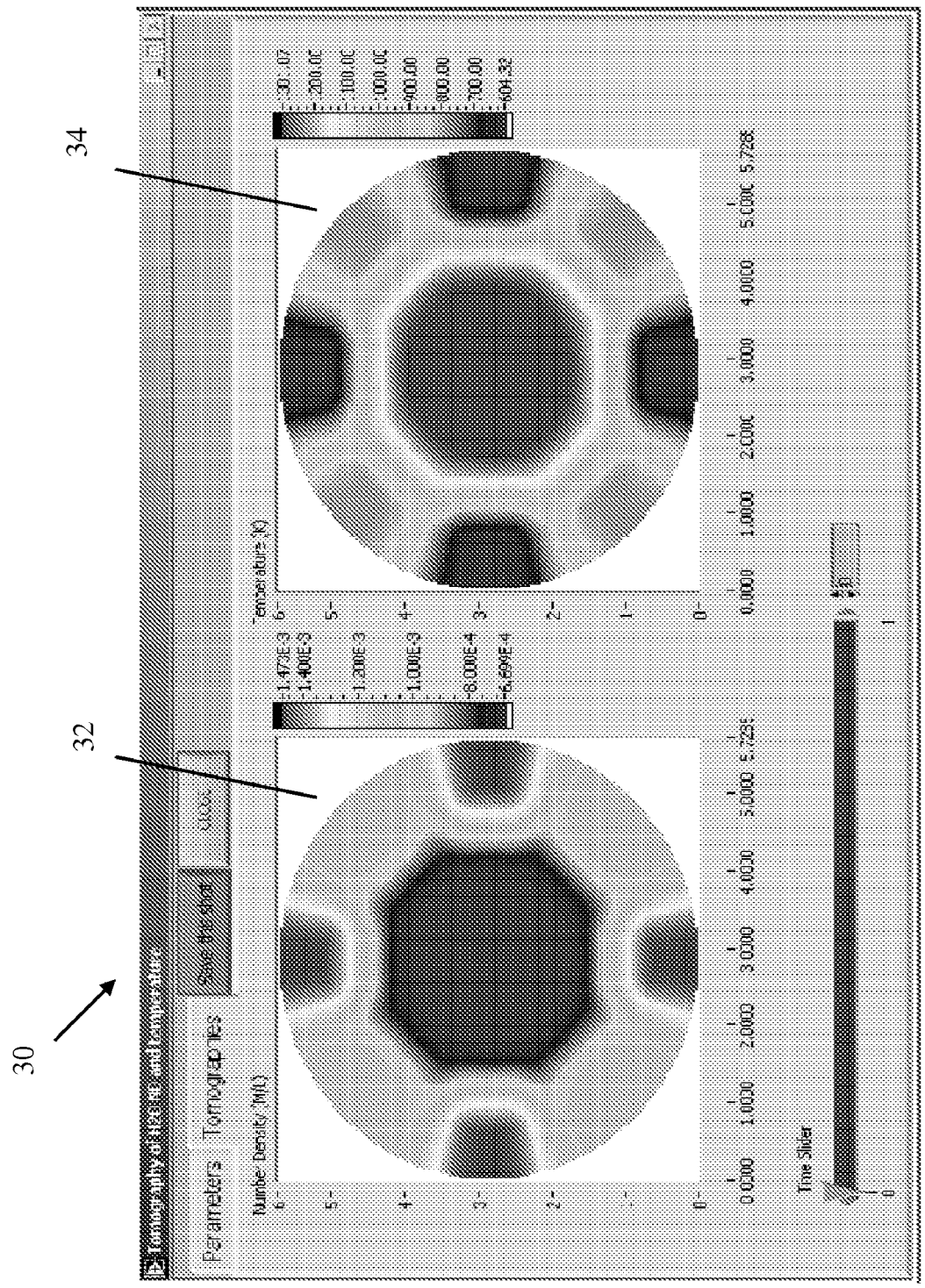
FIGS. 4-5 are representative tomographies derived with the methods described herein.

Example 1 considers a cylindrically symmetric combustion zone measurement using 3 paths and measurement of 3 absorption lines of water, as illustrated in FIGS. 3-4. Thus, in Example 1, temperature and water concentration are measured over a combustion zone 18 having a circular cross section. The temperature and water concentration distributions are assumed to be circularly symmetric. The smallest unit of symmetry employed is one-eighth of the circle. Each symmetrical unit is assumed to exhibit mirror symmetry with respect to the adjacent symmetrical units. Therefore, the temperature and water concentration distribution in only one unit may be determined and the results are assumed to be the same for other units based upon the foregoing assumptions of symmetry. As shown in FIG. 3, three line-of-sight laser paths 20, 22, 24 are deployed at a 22.5 degree separation within a 45-degree arc. Since spectroscopic examination of three wavelengths is made along each path, two bins may be determined along each path; the two bins are assumed to be a boundary bin 26 and central bin 28. Further, the central bin 28 is assumed to have the same size, temperature and water concentration for all three paths according to the underlying assumptions stated above. Correspondingly, the three boundary bins 24 (one bin per path) are each of the same size. With the additional assumption of complete symmetry, each of the three boundary bins may be equally divided into two parts for example 26(a,b), one part being placed at each end of a given path.

Accordingly, there are four bins (three boundary and one central) having four temperatures (T1, T2, T3, and Tc) and one water concentration (x) assuming a partial pressure is equal over the combustion zone and one size of the center bin (Lc). Consequently, this example, based upon the stated assumptions presents six unknowns. Three spectral lines measured along each of the three paths create 9 equations. Thus, the unknowns may be well solved through a minimum-square error or similar method.

With the binning solved, areas off the paths in the explored zone may be mapped by extrapolating from the bin values. For example, on each path, the bin values close to the cross point of the central and boundary bins may be smoothed with a quadratic curve or other technique that ends on the two bin values. Similarly, the area between paths, for example paths 20 and 22 may be divided into two identical parts and the part adjacent to path 20 mapped with bin values derived on path 20 and the part adjacent to path 22 mapped with bin values derived on path 22. In the area coaxial to the break line between the two parts values may be generated with a quadratic curve or other smoothing technique that ends on the two bin values. The same mapping methods are applied to the area between path 22 and 24. The unit may then be symmetrically mapped to the whole circular zone 18.

FIG. 4 is a computer derived representative tomography 30 based upon the foregoing example, showing species concentration 32 and temperature distribution 34. It may be noted that the resolution achieved by the combined use of binning and tomography exceeds the resolution possible with either technique alone.

Example 2

This example is representative of a 3×3 grid measurement of temperature and water concentration in a shock tunnel.

Figure 5:
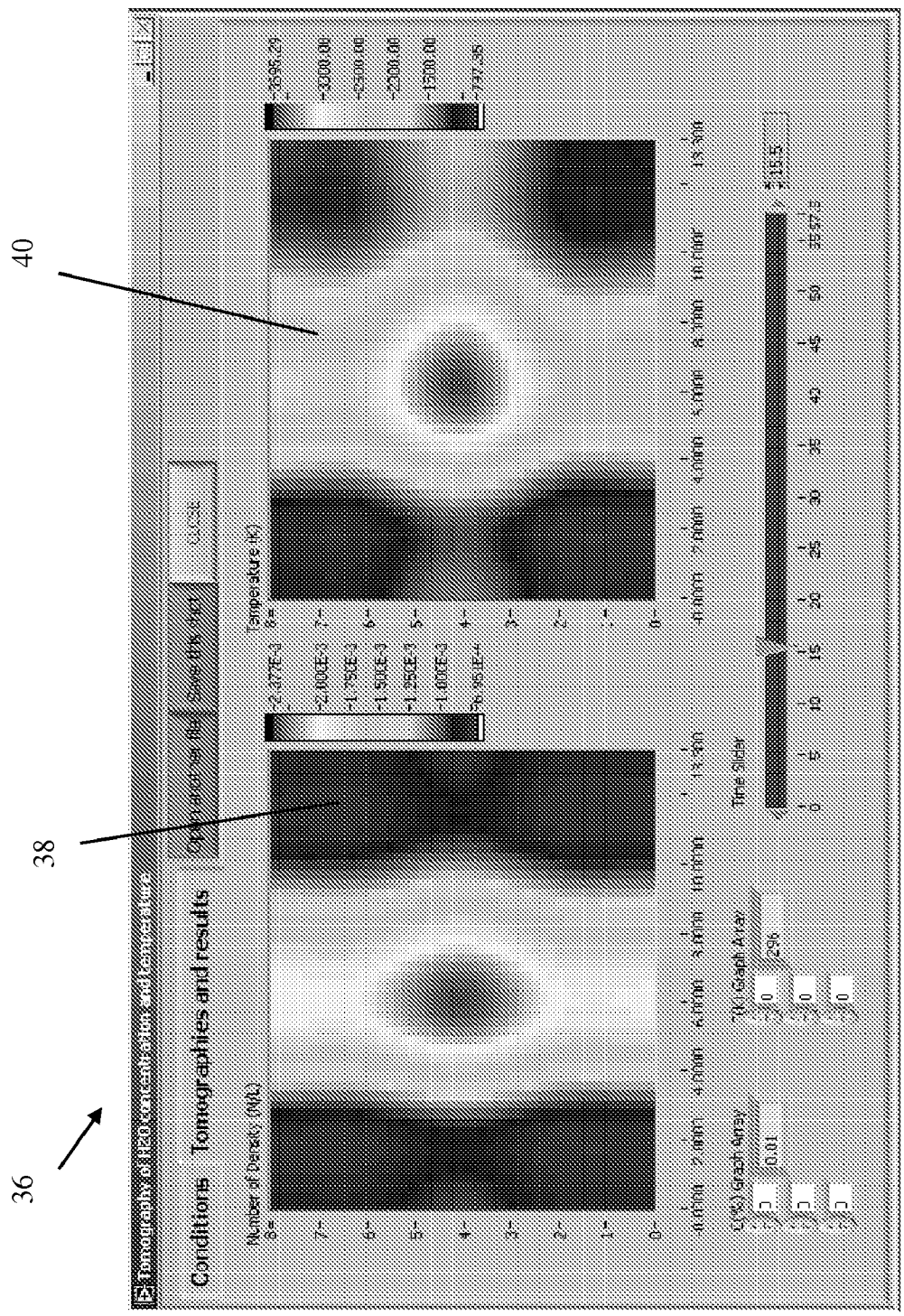

The 3×3 path layout 10 of FIG. 1 is employed in Example 2. Two spectral lines are analyzed along each path. Thus, there exist only 12 analytical functions of position available while the number of unknowns exceeds 12. Therefore it is initially assumed that there is only one temperature and one water concentration along each path. Tomography is based on weighted average over the paths. FIG. 5 is a representative tomography 36 showing species concentration 38 and temperature distribution 40 derived using the techniques described above and based upon the listed assumptions.

Example 3

Figure 6:
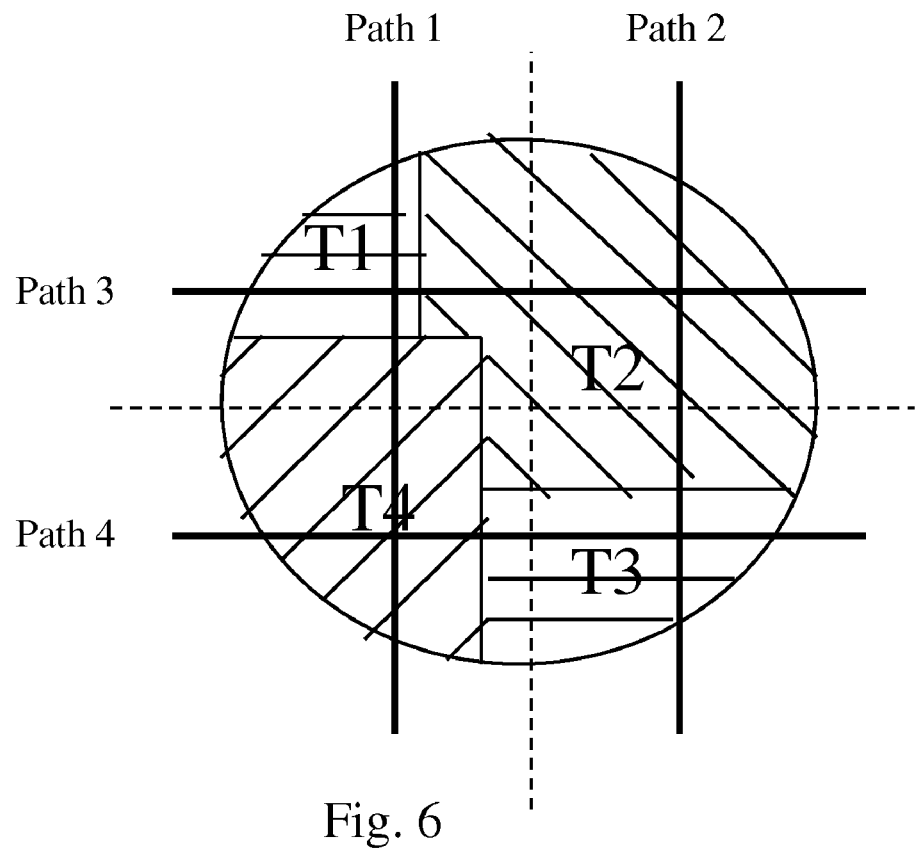
FIGS. 6-16 are alternative line-of-sight path configurations defining select zones for implementation of the methods described herein.
Figure 7:
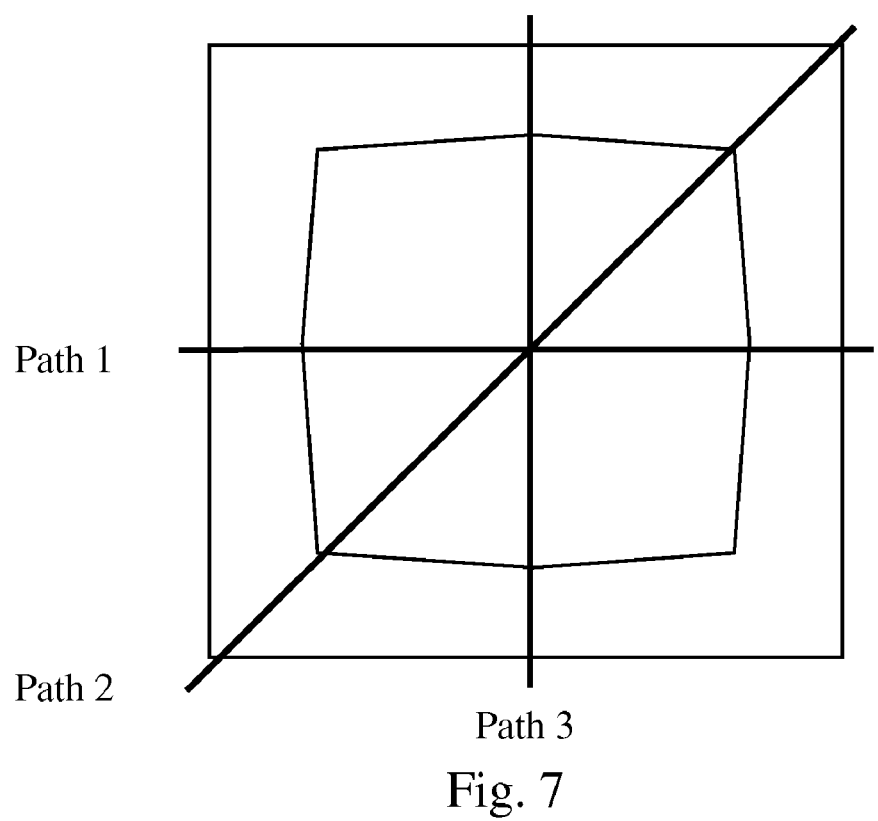
Figure 8:
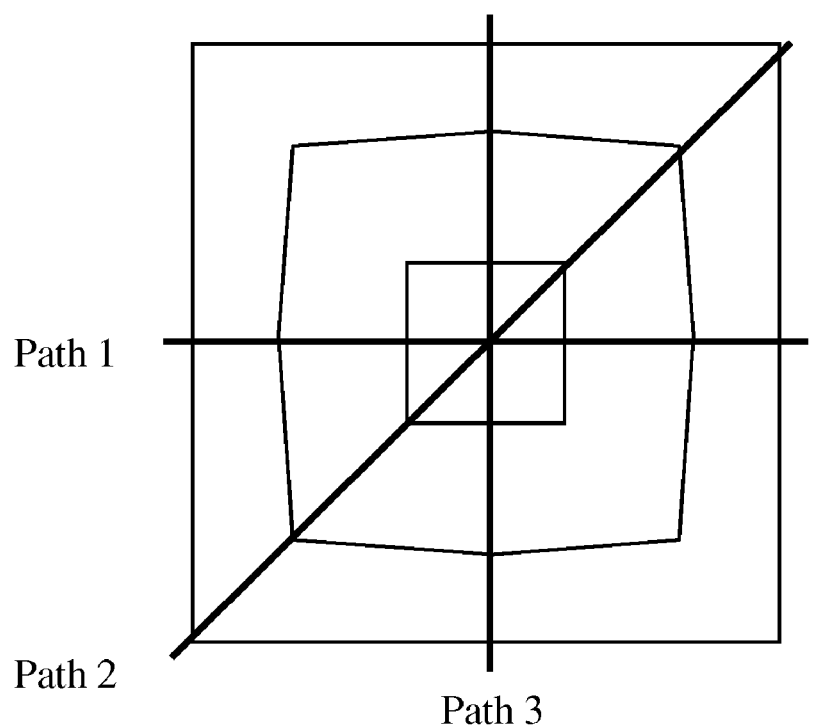
Figure 9:
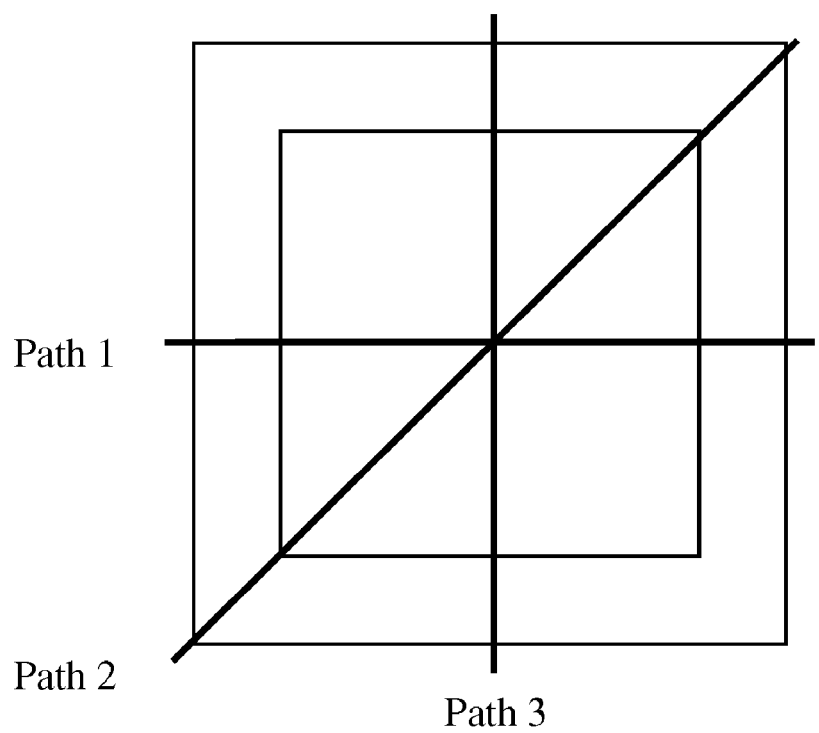
Figure 10:
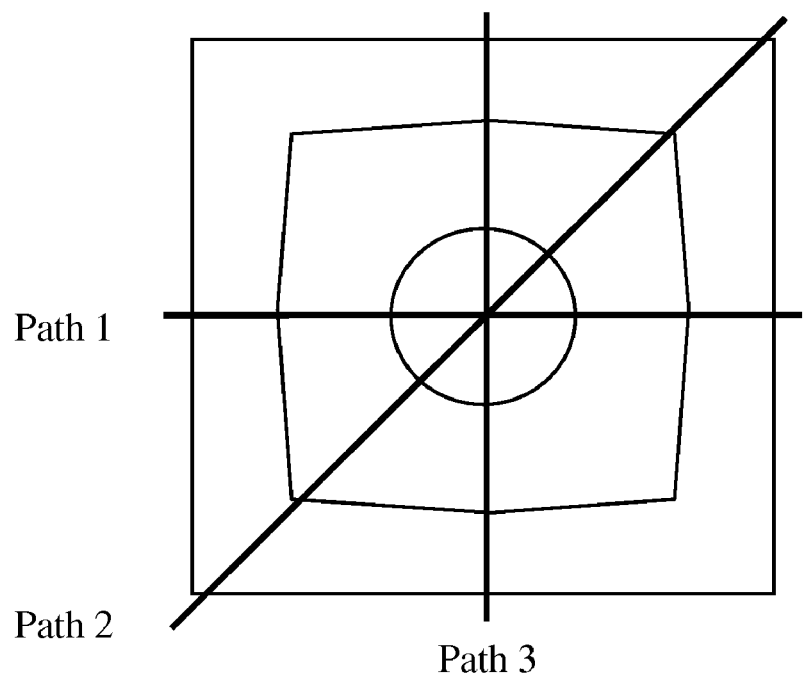
Figure 11:
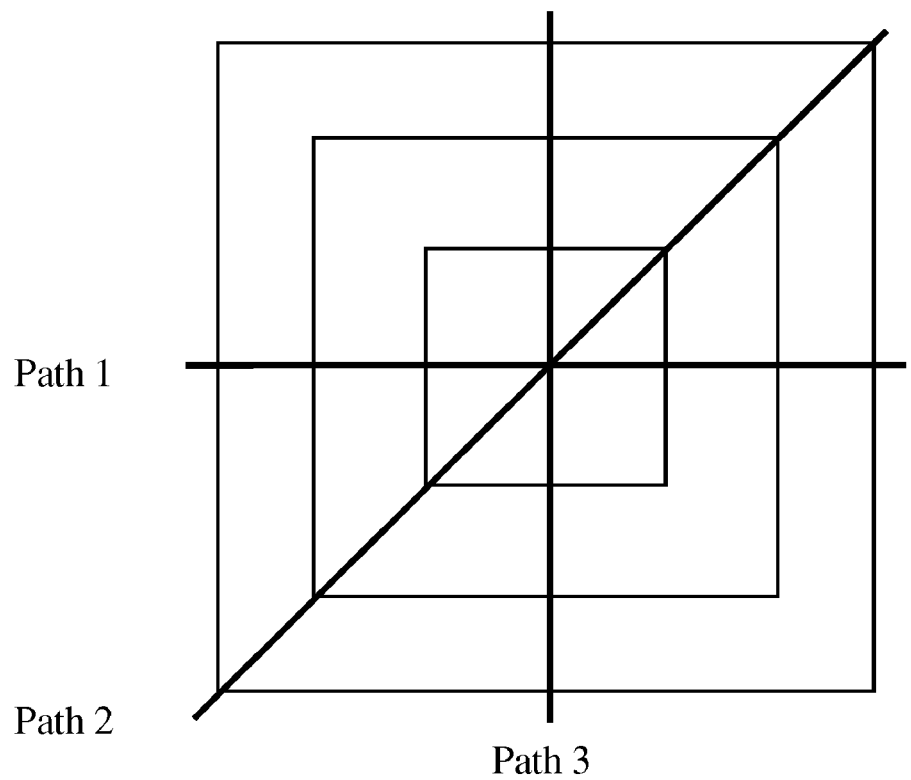
Figure 12:
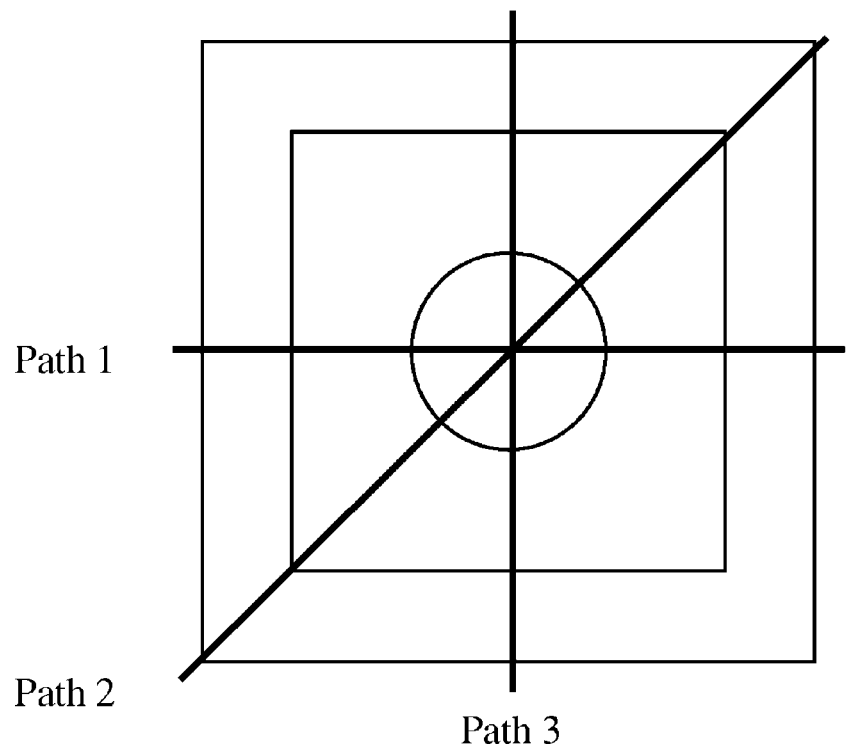
Figure 13:
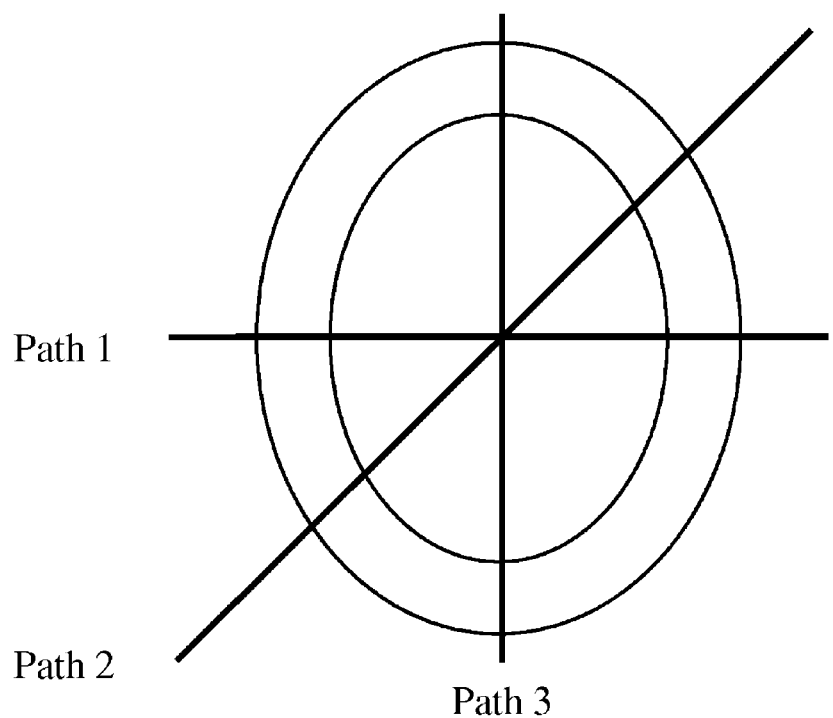
Figure 14:
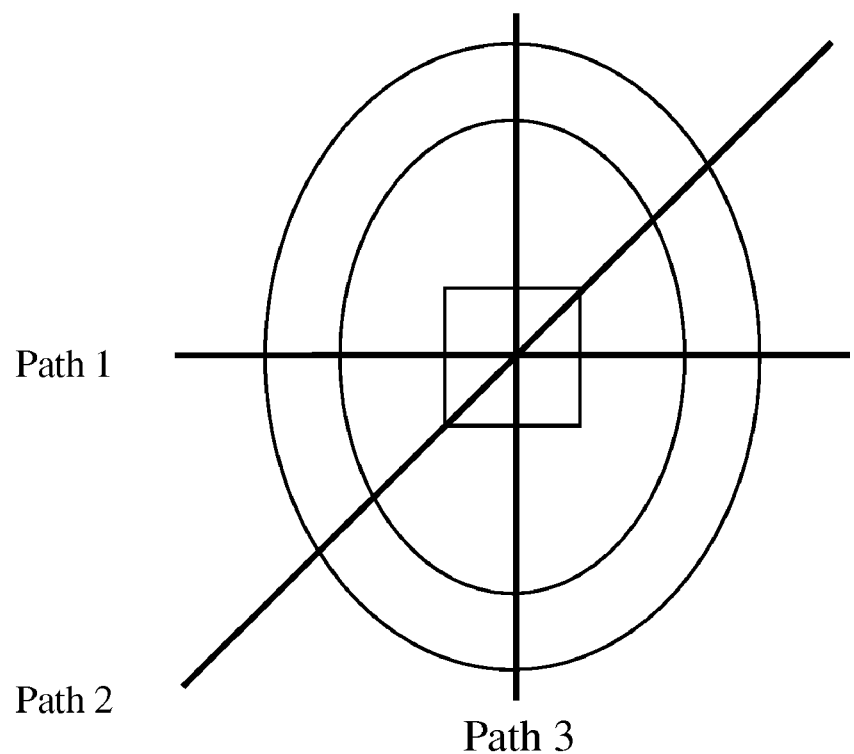
Figure 15:
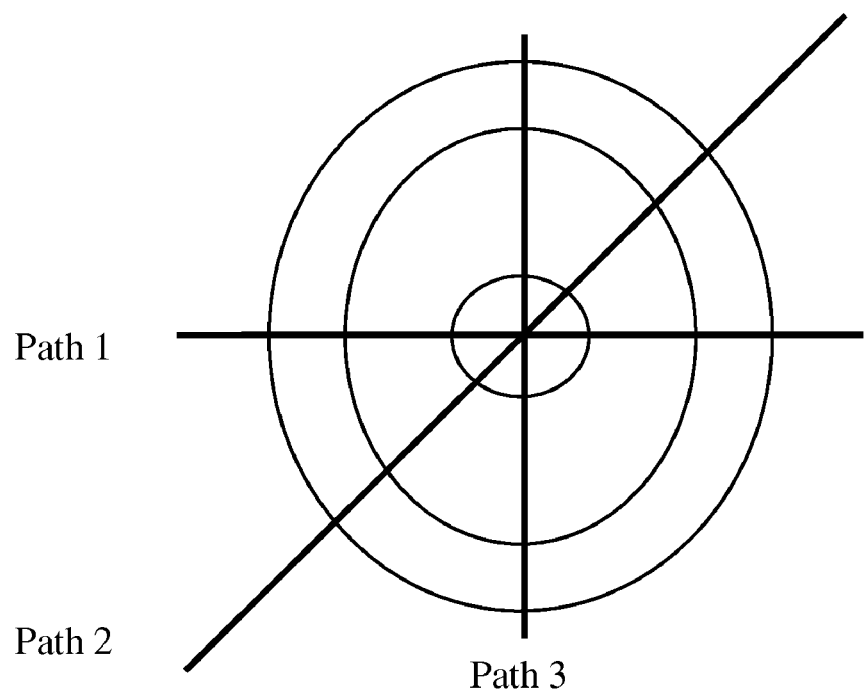

The 2×2 path layout of FIG. 6 represents a 2×2 grid measurement of temperature and water concentration over a circular zone together with the bin/tomography. In this example, three spectral lines are employed per path. Thus there are 12 equations available for analysis. Four bins are assumed each covering one cross point in FIG. 6. They also together form the tomography. In FIG. 6, the figure four bins are denoted as T1, T2, T3 and T4, respectively.

Example 4

Select three-path examples are graphically illustrated in FIGS. 7-15.

Example 5

As described in detail above, in certain instances discrete values and analytical expressions may be combined for solution.

Figure 16:
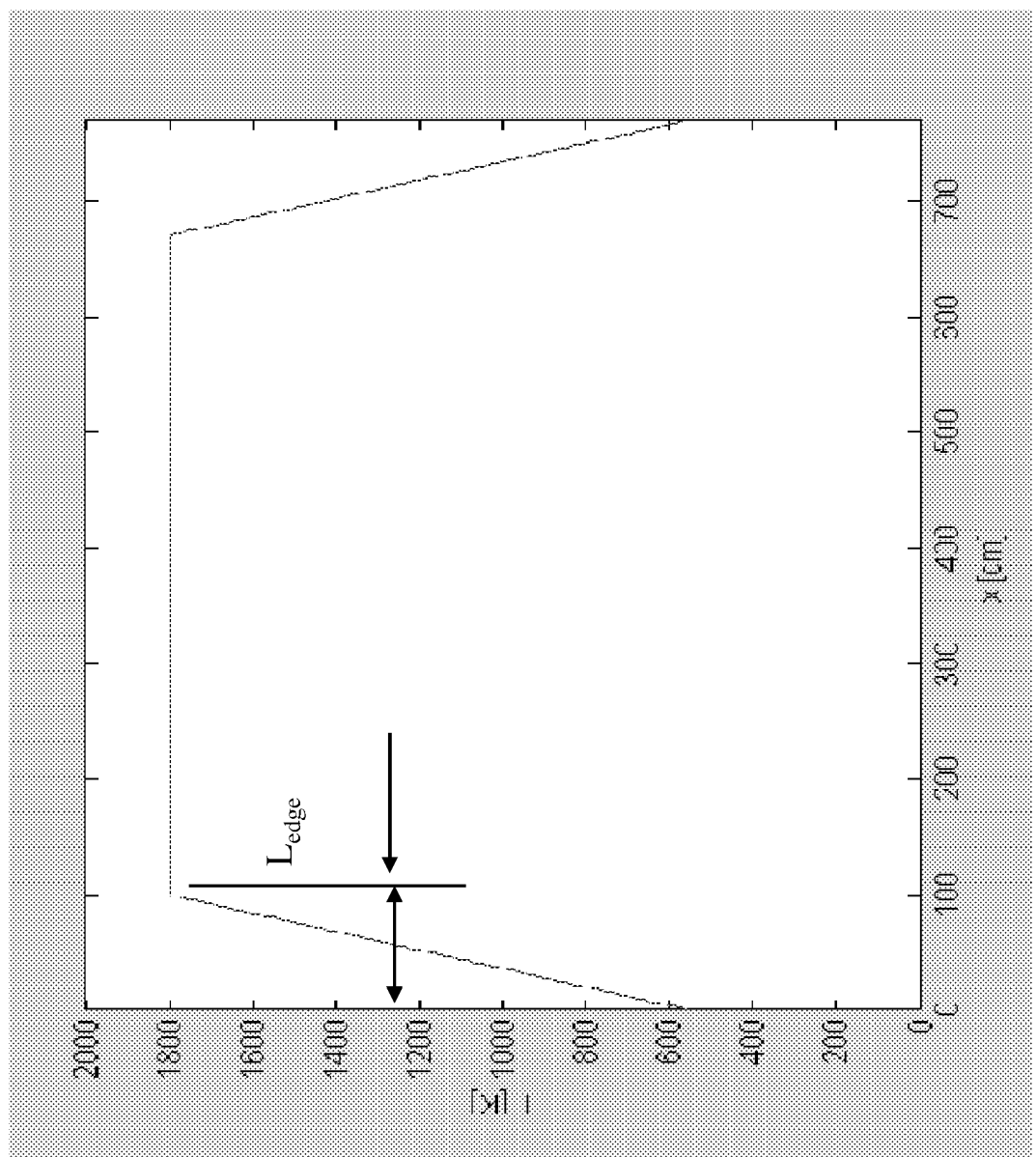

The path illustrated in FIG. 16 is assumed trapezoidal. Each end of it is represented with a slope and the central portion with a constant. The slopes for both ends are identical. Temperature and water concentration are measured. Five spectral lines are employed. The measurement is implemented over selected path locations on a commercial boiler. The bin length is assumed and it is further assumed that only the temperature at the end of the path (the wall temperature) and the temperature at the center and water concentration over the path need to be determined Table 1 shows the result of assuming Ledge/L=0.01 for select paths and table 2 shows the result of assuming Ledge/L=0.1 for a couple of paths.

TABLE 1

Result of assuming $L_{edge}/L = 0.01$ for select paths
$L_{edge}/L = 0.01$

| Path # | $T_{main}$ [K] | $T_{wall}$ [K] | $P_{H2O}$ [atm] |
|---|---|---|---|
| 5 | 1599 | 342 | 0.132 |
| 6 | 1641 | 342 | 0.135 |
| 7 | 1621 | 342 | 0.134 |
| 8 | 1525 | 338 | 0.130 |
| 9 | 1599 | 343 | 0.130 |
| 10 | 1601 | 345 | 0.128 |

TABLE 2

Result of assuming $L_{edge}/L = 0.1$ for a couple of paths
$L_{edge}/L = 0.1$

| Path # | $T_{main}$ [K] | $T_{wall}$ [K] | $P_{H2O}$ [atm] |
|---|---|---|---|
| 5 | 1690 | 320 | 0.144 |
| 6 | 1737 | 320 | 0.148 |
| 7 | 1715 | 320 | 0.146 |
| 8 | 1610 | 316 | 0.141 |
| 9 | 1690 | 322 | 0.141 |
| 10 | 1694 | 324 | 0.139 |

Figure 17:
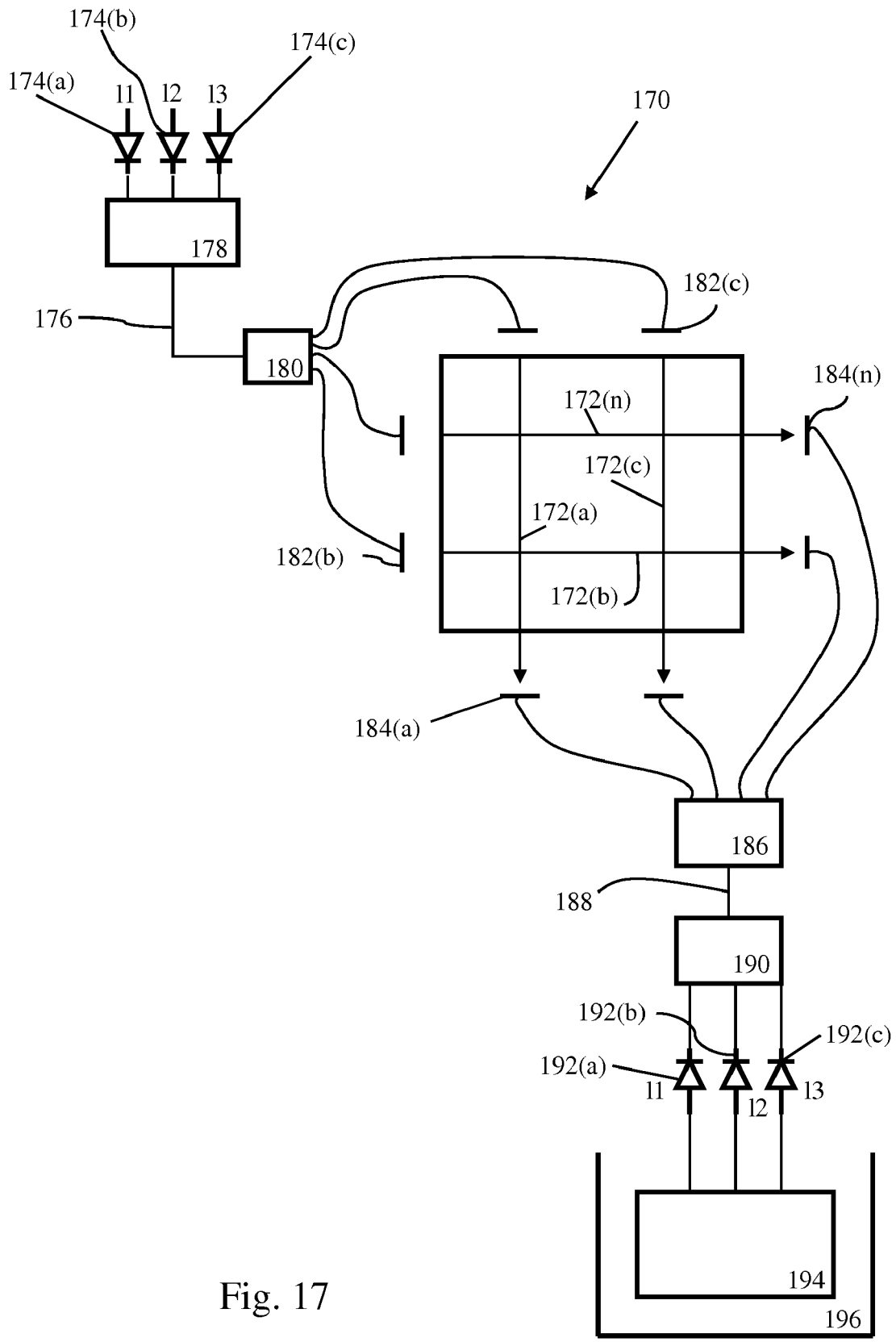
FIG. 17 is a schematic diagram of an apparatus consistent with the present invention.

As is shown in the schematic illustration of FIG. 17, another aspect of the invention disclosed herein is an apparatus for absorption spectroscopy 170 suitable for implementation of the methods described herein. The apparatus for absorption spectroscopy 170 includes apparatus for obtaining absorption data at multiple wavelengths along more than one line-of-sight path 172a-172n through a quantity of gas of interest. The absorption spectroscopy apparatus 170 may include multiple tunable diode laser light sources 174a-174n generating light at multiple wavelengths of interest. The laser light generated at multiple wavelengths may be distributed to the multiple line-of-sight paths 172a-n by any means known in the optical or photonic arts. One representative distribution method is graphically illustrated in FIG. 17. In the FIG. 17 embodiment, light at each wavelength $\lambda_1$-$\lambda_n$ is initially multiplexed and coupled to a single optical fiber 176 by means of multiplexer 178. The optical fiber 176 carrying multiplexed light is coupled to a switch or router 180 which may selectively route the multiplexed light to input or pitch optics 182a-n associated with the input side of each line-of-sight path 172. Light is projected across the line-of-sight path from the input optic 182 to an output or catch optic 184a-n opposite the quantity of gas of interest. Each catch or output optic 184 may be coupled to an output side router or switch 186 which is in communication via an optical fiber 188 with a demultiplexer 190. The output from the demultiplexer may be carried to a series of detectors 192-192n sensitive to the input wavelengths $\lambda_1$-$\lambda_n$. Output from the detectors 192a-n may be communicated to apparatus 194 configured to calculate absorption spectroscopy data. The apparatus 194 may be part of a larger data processing system 196 containing hardware and software suitable for creating a map of temperature and gas species concentration having at least two-dimensional information derived from select temperature and gas species concentration bins identified along the more than one line-of-sight paths 172a-n through the quantity of gas of interest.

The particular optical/photonic configuration of the absorption spectroscopy apparatus 170 described immediately above is representative only. The scope of the invention includes any apparatus suitable for carrying out the methods described herein.

The disclosure also encompasses all possible permutations of the claim set, as if they were multiple dependent claims.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A method of absorption spectroscopy comprising:
   obtaining absorption data at multiple wavelengths along more than one line-of-sight path through a quantity of a gas of interest;
   identifying more than one temperature and gas species concentration bin along multiple line-of-sight paths; and
   creating, using a processor, a map of temperature and gas species concentration, said map having at least two dimensional information derived from select temperature and gas species concentration bins identified along more than one line-of-sight path.

2. The method of absorption spectroscopy of claim 1 further comprising determining the spatial location of a select temperature and gas species concentration bin by comparing the bins identified along one line-of-sight path with the bins identified along an intersecting line-of sight path.

3. The method of absorption spectroscopy of claim 1 wherein the distribution of temperature and species concentration is expressed as an analytical function of position corresponding to each of at least two line-of sight paths.

4. The method of absorption spectroscopy of claim 1 wherein the distribution of temperature and species concentration is expressed as a series of discrete values along at least two line-of sight paths.

5. The method of claim 3 wherein the coefficients of an analytical function of position are solved by applying absorption equations to measured spectral absorptions.

6. The method of claim 3 wherein the coefficients of an analytical function of position are solved by fitting the measured spectral absorptions to spectral profiles calculated with unknown binning parameters.

7. The method of claim 4 wherein the discrete values are determined by applying absorption equations to measured spectral absorptions.

8. The method of claim 4 wherein the discrete values are determined by fitting the measured spectral absorptions to calculated from unknown binning parameters.

9. An apparatus for absorption spectroscopy comprising:
   means for obtaining absorption data at multiple wavelengths along more than one line-of-sight path through a quantity of a gas of interest;
   means for identifying more than one temperature and gas species concentration bin along multiple line-of-sight paths; and
   means for creating a map of temperature and gas species concentration, said map having at least two dimensional information derived from select temperature and gas species concentration bins identified along more than one line-of-sight path.

* * * * *